United States Patent [19]
Ageland et al.

[11] Patent Number: 6,107,467
[45] Date of Patent: Aug. 22, 2000

[54] PROCESS FOR PURIFYING A COMPOUND

[75] Inventors: Hans Ageland, Bromma; Lena Nyström, Stockholm; Josefine Persson, Lund; Folke Tjerneld, Malmö, all of Sweden

[73] Assignee: Pharmacia & Upjohn AB, Stockholm, Sweden

[21] Appl. No.: 08/924,869

[22] Filed: Sep. 5, 1997

Related U.S. Application Data

[60] Provisional application No. 60/026,739, Sep. 26, 1996.

[30] Foreign Application Priority Data

Sep. 11, 1996 [SE] Sweden ................................ 9603304

[51] Int. Cl.$^7$ ............................ C07K 1/14; C07K 14/775
[52] U.S. Cl. ........................ 530/359; 530/412; 530/421; 530/422; 530/424; 435/69.1
[58] Field of Search ..................................... 530/412, 421, 530/422, 424, 359, 350; 435/69.1

[56] References Cited

FOREIGN PATENT DOCUMENTS

WO96/04556   2/1996   WIPO .

OTHER PUBLICATIONS

File Medline on STN. No. 81247630. Fukushima et al. Proceedings of the National Academy of Sciences of the United States of America. vol. 78, No. 5, ppp 2732–2736. Abstract only, 1981.

Garg et al. 'Use of Temperature–Induced Phase Forming Detergent (Triton X–114) as Ligand Carrier for Affinity Partitioning in a Aqueous Three–Phase System', Biotechnol. Appl. Biochem. vol. 20, pp. 199–215, 1994.

Harris et al. 'Enzyme Purification Using Temperature Induced Phase Formation', Bioseparation vol. 2, pp. 237–246, 1991.

Calabresi et al. 'Molecular Characterization of Native and Recombinant Apolipoprotein A–I Milano Dimer', J. of Biol. Chem. vol. 269, No. 23, pp. 32168–32174, Dec. 23, 1994.

Database Caplus on STN. No. 1995:421793. Soma et al. 'Recombinant Apolipoprotein A–Imilano Dimer Inhibits Carotid Intimal Thickening Induced by Pervascular Manipulation in Rabbits', Cir. Res. vol. 76, No. 3, pp. 405–411, 1995.

*Primary Examiner*—Christopher S. F. Low
*Assistant Examiner*—Anish Gupta
*Attorney, Agent, or Firm*—Dinsmore & Shohl LLP

[57] ABSTRACT

The present invention relates to a process for purifying a hydrophobic or amphiphilic compound, by first mixing a starting material containing the hydrophobic or amphiphilic compound with a first polymeric material, water and at least one of a second polymeric material and a surfactant, wherein the first polymeric material and the second polymeric material and/or surfactant are immiscible in the resulting primary aqueous solution. The process further comprises maintaining the primary aqueous solution for a period of time sufficient for essentially separating the phases formed, and then removing the phase containing the main portion of the hydrophobic or amphiphilic compound and the second polymeric material and/or surfactant. The second polymeric material and/or surfactant are separated from the hydrophobic or amphiphilic compound, and subsequently recycled to the initial mixing step. The present invention further relates to a composition for use in purification of apolipoprotein A (ApoA) or apolipoprotein E (ApoE), said composition comprising a first polymeric material and a surfactant, said first polymeric material and surfactant being immiscible in the primary aqueous solution obtained after mixing with water. ApoA or ApoE produced by the inventive process can be used for the manufacture of a medicament in the treatment of atherosclerosis and cardiovascular diseases, sepsis or peripheral atherosclerosis as well as in a method for treatment of atherosclerosis and cardiovascular diseases, sepsis or peripheral atherosclerosis when administered in a therapeutically effective amount.

32 Claims, 1 Drawing Sheet

PROCESS FOR PURIFYING A COMPOUND

This application claims benefit of provisional application 60/026,739 filed Sep. 26, 1996.

FIELD OF THE INVENTION

The present invention relates to a process for purifying a hydrophobic or amphiphilic compound by mixing a starting material containing the target compound, a first polymeric material, water and at least one of a second polymeric material and a surfactant. After separation in two steps, the target compound is recovered while the second polymeric material and/or surfactant are recycled to the mixing step. More particularly, the starting material is a fermentation broth obtained from recombinant production by DNA techniques, and the target compound is apolipoprotein A or apolipoprotein E, produced by such techniques.

BACKGROUND OF THE INVENTION

Aqueous two-phase systems have widespread use in biochemistry and biotechnology for purifying biological materials such as cells, proteins, nucleic acids and steroids (see e.g. P.-Å. Albertsson, Partition of cell particles and macromolecules, 3rd ed., Wiley, New York City, N.Y., USA (1986) and H. Walter et al, Partitioning in Aqueous Two-Phase Systems, Academic Press, Orlando, Fla., USA (1985)). The systems are suitable for biological materials because each phase contains about 70 to 90% by weight of water, thereby substantially reducing the risk of denaturation of biomolecules such as proteins (H. Walter et al, Aqueous two-phase systems, Methods in Enzymology, vol. 228, Academic Press, San Diego, Calif., USA (1994)).

The aqueous two-phase systems are composed of two immiscible polymeric materials, one polymeric material in combination with a high salt concentration or one polymeric material in combination with a surfactant. Elevating the concentrations above a certain critical value produces two immiscible aqueous phases in which the polymeric materials, polymeric material and salt or polymeric material and surfactant are partitioned.

The partitioning of proteins in aqueous two-phase systems mainly depends upon protein hydrophobicity, charge and size. The partitioning can be influenced by changing polymeric materials, the molecular weight of the polymeric materials, the pH and by adding salts to the system (G. Johansson, Acta Chem. Scand., B 28 (1974), pp. 873–882).

Aqueous two-phase systems can be scaled up readily, since the partitioning of biological materials such as proteins is essentially independent of the size of the system. The time for phase separation can, however, be prolonged in large-scale systems depending e.g. on the geometry of the separation vessel.

On a laboratory scale, use is commonly made of dextran and polyethylene glycol (PEG) as the immiscible polymeric materials. Dextran is, however, a relatively expensive polymeric material and for large-scale purification, e.g. industrial scale enzyme extraction, various combinations of PEG and salts are more frequent (K. Köhler et al, Methods in Enzymology, vol. 228, Academic Press, Orlando, Fla., USA, (1994), pp. 627–640).

U.S. Pat. No. 4,740,304 to Perstorp AB relates to compositions containing hydroxy-alkyl starch for use in systems with two or more phases for extraction, purification, concentration and/or separation of biological substances. In one preferred embodiment, the hydroxyalkyl starch is hydroxypropyl starch (HPS). In another preferred embodiment the hydroxyalkyl starch is combined with another polymer, e.g. polyethylene glycol (PEG) or polypropylene glycol. In the examples of U.S. Pat. No. 4,740,304, use is made of various enzymes.

The use of aqueous two-phase systems for purifying biomolecules has been limited, however, since the target products have been contaminated with a phase-system polymer, thus necessitating additional and complicated purification steps. Thus, hitherto the target products to be purified have been partitioned to a salt solution or remained dissolved together with a phase-system polymer. To alleviate this problem, the use of thermo-separating polymeric materials in aqueous two-phase systems has been introduced. This makes it possible to perform temperature-induced phase separation whereby the target biomolecule can be separated from the polymeric material in a very efficient way. This technique has been utilized on a laboratory scale for purifying various enzymes. Thus, temperature-induced phase separation has been used to purify 3-phosphoglycerate kinase and hexokinase from baker's yeast homogenate (P. A. Harris et al, Bioseparation, vol. 2 (1991) pp. 237–246). Furthermore, temperature-induced phase separation has been used to purify two ecdysteroids and glucose-6-phosphate dehydrogenase (P. A. Alred et al, J. Chromatogr., vol. 628 (1993) pp. 205–214 and P. A. Alred et al, Bioseparation, vol. 2 (1992), pp. 363–373, respectively). P. A. Alred et al, J. Chromatogr. A, 659 (1994) pp. 289–298, also discloses temperature-induced phase separation for purifying glucose-6-phosphate dehydrogenase, hexokinase and 3-phosphoglycerate kinase from baker's yeast.

EP-A-262651 to Union Carbide relates to a method for recovering enzymes from aqueous solutions which contains at least one polymeric material exhibiting inverse solubility characteristics. The method comprises elevating the temperature of the solution above the temperature of precipitation of the polymeric material and separating the polymeric precipitate from the enzyme-containing solution. The polymeric material is preferably selected from polyalkylene glycols, such as polyethylene or polypropylene glycol, poly (oxyalkylene) polymers or copolymers, ethoxylated surfactants, silicone-modified polyethers and polyvinyl pyrrolidone. The temperature is suitably elevated to a temperature less than about 90° C. preferably between about 50° C. and about 75° C. In the examples of EP-A-262651, use is made of λ-amylase.

EP-A-0 574 050 to Gist-Brocades relates to large-scale separation and purification of hydrophobic fermentation products. The method comprises adding to a mixture of the desired product and contaminants a non-ionic surfactant, a flocculating agent, an extra surfactant and a salt. The fermentation product is suitably a protein and preferably an enzyme, which can be used in detergent compositions.

WO 96/23061 to Genencor International relates to a surfactant-based enzyme extraction process, wherein a hydrophilic fermentation product, especially a detergent-type enzyme, is purified by contacting a clarified or whole fermentation broth containing the desired product with one or more salt(s) and a suitable surfactant with a HBL value exceeding about 12. The fermentation broth, salt and surfactant are separated into two phases, one of which is rich in surfactant and the desired product and the other rich in salt(s).

Garg et al, Biotechnol. Appl. Biochem. 20 (1994) pp. 199–215 relates to use of a temperature-induced phase-forming detergent (Triton X-114) as ligand carrier for affinity partitioning in an aqueous three-phase system. Triton X-114 was modified with Cibacron Blue to give a detergent-dye conjugate, which was used as an affinity ligand for the enzyme lactate dehydrogenase (LDH). When an excess of detergent was used, a three-phase system with a detergent-rich middle phase was formed. The detergent-dye conjugate partitioned to this detergent-rich phase. The enzyme was recovered by harvesting the detergent-rich conjugate-containing phase and subjecting it to temperature-induced phase separation.

As is evident from the above, the use of two-phase separation has been directed primarily to purification of hydrophilic macromolecules, in particular enzymes. Use of two-phase systems for purifying hydrophobic lipoproteins, is, however, known. Thus, Wiegel et al relates to partitioning of high-density lipoproteins (HDL) in two-phase systems (J. Chromatogr. B, 661 (1994) pp. 159–164). Here use is made of dextran and PEG for separating the HDL particles. The preferred enrichment of HDL particles in the dextran-rich more hydrophilic bottom phase is attributed to hydrogen bonding between dextran and the molecules constituting the HDL particles (the apo-protein of HDL).

The main function of lipoproteins in plasma is to transport lipids, such as cholesterol and triglycerides. There are four major classes of lipoproteins: chylomicrons (CM), very low density (VLDL), low density (LDL) and high density (HDL) lipoproteins. Of these, HDL is directly involved in the removal of cholesterol from peripheral tissues, carrying it back either to the liver or to other lipoproteins, by a mechanism known as "reverse cholesterol transport" (RCT).

The "protective" role of HDL has been confirmed in a number of studies. Recent studies directed to the protective mechanism(s) of HDL have been focused on apolipoprotein A-I (ApoA-I), the major component of HDL. High plasma levels of ApoA-I are associated with a reduced risk of CHD and presence of coronary lesions.

Several methods have been proposed for purifying lipoproteins, such as ApoA and ApoE, either from plasma or produced by recombinant DNA techniques. On a laboratory scale use is commonly made of centrifugation, ion-exchange chromatography, affinity chromatography, isoelectric focusing, gel filtration and high-performance liquid chromatography (HPLC) (see Methods in Enzymology, vol. 128, Academic Press, San Diego, Calf., USA (1986)). There is, however, a need for an additional quick, sensitive and reliable method for preparation of ApoA and ApoE, especially on an industrial or pilot-plant scale.

As stated previously, the use of two-phase separation has been directed primarily to purification of hydrophilic macromolecules. Optimization of the two-phase separation technique for purifying hydrophobic or amphiphilic compounds, would increase the number of process techniques available for purifying the hydrophobic or amphiphilic compounds, e.g. lipoproteins such as ApoA or ApoE. It is the purpose of the present invention to provide such a technique.

SUMMARY OF THE INVENTION

The present invention relates to a process for purifying a hydrophobic or amphiphilic compound, by first mixing a starting material containing the hydrophobic or amphiphilic compound with a first polymeric material, water and at least one of a second polymeric material and a surfactant, wherein the first polymeric material and the second polymeric material and/or surfactant are immiscible in the resulting primary aqueous solution. The process further comprises maintaining the primary aqueous solution for a period of time sufficient for essentially separating the phases formed, and then removing the phase containing the main portion of the hydrophobic or amphiphilic compound and the second polymeric material and/or surfactant. The second polymeric material and/or surfactant are separated from the hydrophobic or amphiphilic compound, and subsequently recycled to the initial mixing step. The present invention further relates to a composition for use in purification of apolipoprotein A (ApoA) or apolipoprotein E (ApoE), said composition comprising a first polymeric material and a surfactant, said first polymeric material and surfactant being immiscible in the primary aqueous solution obtained after mixing with water. ApoA or ApoE produced by the inventive process can be used for the manufacture of a medicament in the treatment of atherosclerosis and cardiovascular diseases, sepsis or peripheral atherosclerosis as well as in a method for treatment of atherosclerosis and cardiovascular diseases, sepsis or peripheral atherosclerosis when administered in a therapeutically effective amount.

BRIEF DESCRIPTION OF THE DRAWING

The present invention will be more fully understood in view of the drawing in which FIG. 1 sets forth a schematic diagram of the inventive process for purifying the hydrophobic or amphiphilic compound according to the procedure described in Example 1.

DETAILED DESCRIPTION OF THE INVENTION

Figure 1:
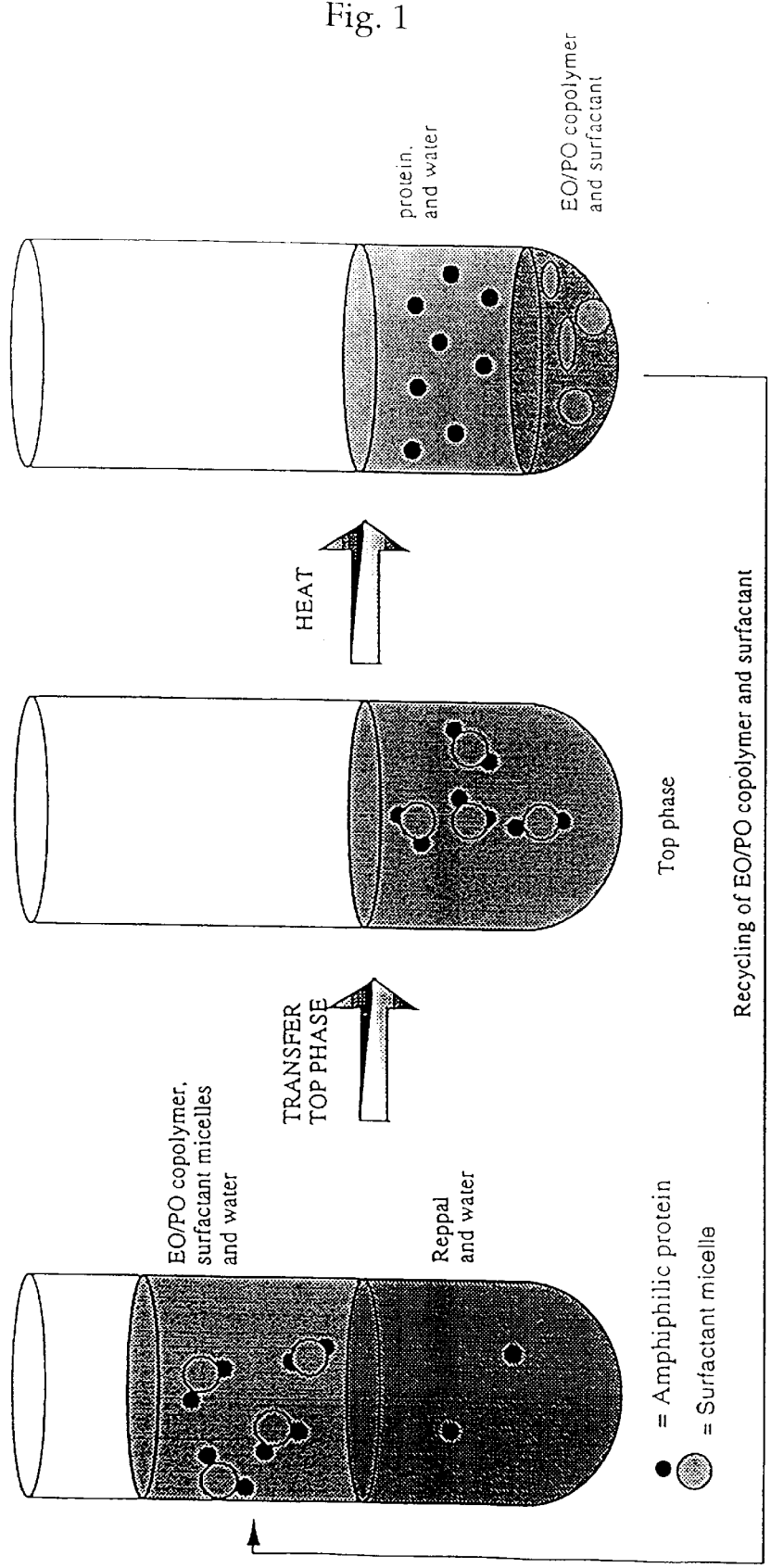

An object of the present invention is to provide an efficient purifying process for producing hydrophobic or amphiphilic compounds with a low enough content of impurities to obviate the need for further purifying steps.

A further object of the present invention is a process providing a high yield of said hydrophobic or amphiphilic compounds, i.e. a process with a minimal loss of product.

Another object of the present invention is to provide an efficient process, where, in the case of biological entities, the biological activity of hydrophobic or amphiphilic compounds are essentially retained.

Yet another object of the present invention is to provide an economical and environmental-friendly process, where a substantial amount of the components are recycled for renewed use.

The objects above are met by the present invention, which relates to a process for purifying a hydrophobic or amphiphilic compound, by a) mixing, in arbitrary order, the starting material containing the hydrophobic or amphiphilic compound, a first polymeric material, water and at least one of a second polymeric material and a surfactant, said first polymeric material and the second polymeric material and/or surfactant being immiscible in the resulting primary aqueous solution, and;

b) maintaining the primary aqueous solution for a period of time sufficient for essentially separating the phases formed;

c) removing the phase containing the main portion of the hydrophobic or amphiphilic compound and the second polymeric material and/or surfactant;

d) separating the hydrophobic or amphiphilic compound from the second polymeric material and/or surfactant; and subsequently e) recycling the separated second polymeric material and/or surfactant to the initial mixing step (a).

A preferred embodiment of the present invention relates to a process for purifying a hydrophobic or amphiphilic compound, by mixing a starting material containing the hydrophobic or amphiphilic compound with a first polymeric material, water and at least one of a second polymeric material and a surfactant, the second polymeric material and/or surfactant exhibiting inverse solubility characteristics, maintaining the resulting primary aqueous solution for a period of time sufficient for essentially separating the phases formed, and removing the phase containing the main portion of the hydrophobic or amphiphilic compound and the second polymeric material and/or surfactant. Subsequently, the hydrophobic or amphiphilic compound is separated from the second polymeric material and/or surfactant by heating the removed phase to a temperature below the temperature where degradation of the hydrophobic or amphiphilic compound occur but above the cloud point of the second polymeric material and/or surfactant for precipitating said second polymeric material and/or surfactant, and thereafter separating the phase containing the precipitated second polymeric material and/or surfactant from the phase containing the hydrophobic or amphiphilic compound.

The present invention provides an economical and environmental-friendly aqueous two-phase process for purifying hydrophobic or amphiphilic compounds, since the second polymeric material and/or surfactant can be recycled several times with only small losses in each cycle, while the purity and yield of the hydrophobic or amphiphilic compound produced according to the present process will be essentially unaltered. In particular, the inventors of the present invention have found that aqueous two-phase separation in combination with temperature-induced phase separation and recycling of one or more process chemical(s) can be used efficiently to purify lipoproteins such as ApoA and ApoE.

With the present invention it is possible to recycle at least about 60% of the initial amount of the second polymeric material and/or surfactant, suitably at least 70% and preferably at least 80% of the initial amount of the second polymeric material and/or surfactant, to the initial mixing step.

The present invention also relates to a composition for use in a primary aqueous solution for purifying apolipoprotein A (ApoA) or apolipoprotein E (ApoE), or variants or mixtures thereof, wherein said composition comprises a first polymeric material and a surfactant, said first polymeric material and surfactant being immiscible in the primary aqueous solution. Preferably, the composition further contains a second polymeric material.

The present invention further relates to use of a composition for purifying apolipoprotein A (ApoA) or apolipoprotein E (ApoE), or variants or mixtures thereof, in a primary aqueous solution, wherein said composition comprises a first polymeric material and a surfactant, said first polymeric material and surfactant being immiscible in the primary aqueous solution.

The present invention further relates to use of ApoA or ApoE produced according to the inventive process for the manufacture of a medicament comprising the ApoA or ApoE in the treatment of atherosclerosis and cardiovascular diseases, sepsis or peripheral atherosclerosis.

The present invention further relates to a method for treatment of atherosclerosis and cardiovascular diseases, sepsis or peripheral atherosclerosis by administering ApoA or ApoE produced according to the inventive process in a therapeutically effective amount.

In the primary aqueous two-phase separation step, use can be made of various combinations of components, i.e. a first polymeric material and a second polymeric material, a first polymeric material and a surfactant, or a first polymeric material, a second polymeric material and a surfactant. In all of these embodiments, the components must be immiscible in the primary aqueous solution. In one embodiment of the present invention, therefore, one polymeric material should be essentially hydrophilic and the other more hydrophobic but still water soluble, i.e. amphiphilic. Also, the concentrations of the first and second polymeric material should be high enough to bring about a phase separation into at least two phases. Examples of hydrophilic, first polymeric materials suitable for use in the present invention include hydroxyalkyl cellulose, hydroxyalkyl starches, starch, dextran, pullulan, and derivatives and mixtures thereof. Pullulan is a microbial polysaccharide previously employed for purifying enzymes in aqueous two-phase systems (Nguyen et al, Appl. Microbiol. Biotechnol., vol. 27 (1988) pp. 341–346). The hydroxyalkyl starches are suitably selected from the group consisting of hydroxymethyl starch, hydroxyethyl starch, hydroxypropyl starch and hydroxybutyl starch, and mixtures thereof. The molecular weight of the hydrophilic, first polymeric material can be in the range of from about 5,000 up to about 5,000,000 Da, suitably in the range of from 40,000 up to 500,000 Da, and preferably in the range of from 100,000 up to 300,000 Da. Specific examples of hydroxyalkyl starches suitable for use in the present invention include Reppal PES 100 and Reppal PES 200, both of which are hydroxypropyl starches marketed by Carbamyl AB of Kristianstad, Sweden. The average molecular weight of Reppal PES 100 and Reppal PES 200 are 100,000 Da and 200,000 Da, respectively.

As stated in the previous paragraph, the second polymeric material shall be amphiphilic and water soluble. The hydrophobic or amphiphilic target compound will be extracted into the more hydrophobic phase and thereby separated from more hydrophilic contaminants such as bulk proteins commonly encountered in plasma and crude or partly purified solutions/fermentation broths from recombinant DNA processes. Examples of such contaminants are proteins from *E. coli*. In the experiments disclosed in the Examples of the present application, the amphiphilic co-polymer and surfactant were partitioned mainly to the top phase. Therefore, in these experiments the main portion of ApoA or ApoE was distributed to the top phase rich in copolymer and surfactant.

In the present invention, the second polymeric material preferably exhibits inverse solubility. The term "inverse solubility" means that the solubility of the polymeric material varies inversely with the solution temperature. This means that the solubility of the polymeric material decreases with increasing solution temperature. Inverse solubility is therefore directly opposed to the temperature effect exhibited by most solutes.

Compositions containing three or more polymeric materials are also within the scope of the present invention. Thus, multi-phase separation can be obtained by selecting suitable combinations of three or more polymeric materials and sufficiently high concentrations thereof in the primary aqueous solution.

In the present invention, the term "primary aqueous solution" relates to the initial separation step before separation into at least two phases, unless otherwise stated.

The primary solution is aqueous, i.e. the main portion of the solvent is water. The water can be added separately or together with any of the components necessary for the primary separation step. Thus, one or more aqueous solutions containing the hydrophobic or amphiphilic compound, first or second polymeric material or surfactant can be used to introduce the component per se as well as the water required to make up the primary aqueous solution.

The concentration of the target compound in the primary aqueous solution can be in the range of from about 0.1 g/l up to about 50 g/l of the primary aqueous solution, suitably within the range of from 0.5 up to 20 g/l, and preferably within the range of from 1 up to 10 g/l.

The concentration of the hydrophilic, first polymeric material in the primary aqueous solution can be in the range of from about 1 up to about 30% by weight of the total weight of the primary aqueous solution, suitably within the range of from 3 up to 20% by weight, and preferably within the range of from 5 up to 15% by weight.

In the primary aqueous solution, the concentration of the amphiphilic, second polymeric material can be in the range of from about 0.5 up to about 30% by weight of the total weight of the aqueous solution, suitably within the range of from 3 up to 20% by weight, and preferably within the range of from 5 up to 15% by weight.

In the primary aqueous solution, the ratio between the concentration of the target compound and the amphiphilic, second polymeric material can be in the range of from about 3:1 to about 1:2,500 calculated by weight, suitably within the range of from 2:3 to 1:400 by weight, and preferably within the range of from 1:3 to 1:150 by weight.

In the primary aqueous solution, the ratio between the concentration of the hydrophilic, first polymeric material and the amphiphilic, second polymeric material can be in the range of from about 20:1 to about 1:10 calculated by weight, suitably within the range from 10:1 to 1:5 by weight, and preferably within the range of from 5:1 to 1:2 by weight.

After mixing the hydrophobic or amphiphilic compound, e.g. ApoA or ApoE, with the first polymeric material and the second polymeric material and/or surfactant, the primary aqueous solution is maintained for a period of time sufficient for essentially separating the at least two phases formed. This period of time can be in the range of from about 2 min up to about 5 hours, suitably in the range of from 5 min up to 2 hours and preferably in the range of from 10 min up to 1 hour. However, the period of time required for phase separation can be reduced by using e.g. centrifugal separation, centrifugal centrifugation or centrifugal decanting, before allowing the primary aqueous solution to separate into the at least two phases. If such means are employed, the period of time for the separation into at least two phases can be in the range of from about 5 sec up to about 60 min, and suitably in the range of from 10 sec up to 30 min.

The temperature of the primary aqueous solution suitably lies in the range of from about 5 up to about 40° C., and preferably in the range of from 15 up to 30° C.

In a further embodiment of the present invention, a compound containing two or three nitrogen atoms bonded to a carbon atom is present in the primary aqueous solution. In this way, an improved purification and yield can be obtained, since the target compound more readily partitions to the more hydrophobic phase. Suitable examples of such nitrogen-containing compounds are urea, arginine, guanidine hydrochloride, benzamidine and mixtures thereof, preferably urea. If used, the concentration of the compound containing two or three nitrogen atoms bonded to a carbon atom should be in the range of from about 0.5 M up to saturation, suitably in the range of from 1 M up to 8 M, and preferably in the range of from 1.5 M up to 6 M.

In the primary aqueous solution, the ratio between the target compound and the nitrogen-containing compound can be in the range of from about 1:1 to about 1:5,000 calculated by weight, suitably within the range of from 1:4 to 1:700 by weight, and preferably within the range of from 1:6 to 1:250 by weight.

The partitioning of the target compound to the more hydrophobic phase can be enhanced by adding a compound with a hydrophobic cation to the primary aqueous solution. Suitable compounds include inorganic salts containing cations such as straight or branched trimethyl ammonium, triethyl ammonium, tripropyl ammonium, tributyl ammonium, tetramethyl ammonium, tetraethyl ammonium, tetrapropyl ammonium, and tetrabutyl ammonium, and anions such as phosphates, sulfate, nitrate, chloride, and hydrogen carbonate. A specific example is triethyl ammonium phosphate.

The partitioning of molecules between the phases of two-phase systems is described by the partitioning coefficient K. It is defined as $$K = C_T/C_B \quad (1)$$

wherein
$C_T$=the concentration in the top phase of the molecule of interest
$C_B$=the concentration in the bottom phase of the molecule of interest.

In many cases the distribution ratio, G, is used in partitioning experiments. This is defined as the ratio between the total amount of partitioned substance in each phase:

$$G = K \times (V_T/V_B) \quad (2)$$

wherein
$V_T$=volume of the top phase
$V_B$=volume of the bottom phase

The partitioning of molecules between the phases of two-phase systems can be shown in phase diagrams. Here, the border line between one and two phases is called the binodial curve. The polymer concentration of the two phases in equilibrium with each other are described by tie lines in the phase diagram. Increasing the polymer concentration, i.e. increasing the tie line length, leads to more extreme partitioning in two-phase systems (G. Johansson, Methods in Enzymology, vol. 228 (1994) pp. 28–42). It lies within the competence of the person skilled in the art to perform experiments for arriving at conditions for suitable partitioning between the two phases.

Two suitable combinations of a hydrophilic, first polymeric material and an amphiphilic, second polymeric material for use in the present invention are Reppal PES 200 in combination with UCON 50-HB-5100 and Reppal PES 200 in combination with $EO_{30}PO_{70}$. Phase diagrams showing the partitioning between the two phases in these systems are given in P. A. Alred et al, Journal of Chromatography, 659 (1994) pp. 289–298, and R. F. Modlin et al, Journal of Chromatography, 668 (1994) pp. 229–236, respectively.

The presence of a surfactant in the primary aqueous solution is intended for increasing the partitioning of the hydrophobic or amphiphilic compound to the more hydrophobic phase. Therefore, the surfactant is suitably an amphiphile, i.e. a compound containing a hydrophilic, water-soluble group facing the aqueous environment, and a hydrophobic, water-insoluble group, facing the hydrophobic or amphiphilic compound. Preferably, the hydrophilic group resembles the chemical structure of the second polymeric material, since this facilitates the partitioning of both the second polymeric material and the surfactant to the top phase of the primary aqueous system.

Amphiphilic surfactants are characterized by the critical micelle concentration (CMC), which is the minimum concentration for the surfactant to form complete micelles. Amphiphiles are furthermore characterized by their hydrophiliclipophilic balance (HLB). The HLB value is a quantitative measure of the overall hydrophilic nature of the surfactant at issue, wherein a higher HLB value means an increased hydrophilic character of the surfactant. In the present invention the HLB value is advantageously in the range of from about 5 up to about 80, suitably in the range of from 8 up to 30, and preferably in the range of from 10 up to 20. Values of the HLB's for a large number of surfactants can be found in McCutcheon's, vol. 1, Emulsifiers and Detergents, North American Ed., 1993.

In a particularly preferred embodiment of the present invention, use is made of a second polymeric material exhibiting inverse solubility. In this case, temperature-induced phase separation is performed following the primary aqueous two-phase step by heating the phase containing the main portion of the hydrophobic or amphiphilic compound to a temperature above the cloud point of the second polymeric material. This phenomenon can be used to advantage in the present invention also with surfactants exhibiting inverse solubility. Thus, by selecting a suitable surfactant and suitable process conditions as regards e.g. the concentration of the various components, pH, ionic strength and temperature, it is possible to separate the surfactant exhibiting inverse solubility from the hydrophobic or amphiphilic compound. In the present invention it is also conceivable to use a combination of a second polymeric material exhibiting inverse solubility and a surfactant exhibiting inverse solubility, where the cloud point can be the same or different for the two components.

Generally, in the present application information pertaining to second polymeric materials exhibiting inverse solubility is equally applicable to surfactants exhibiting inverse solubility.

Examples of surfactants which can be used to advantage in the primary aqueous solution of the present invention include non-ionic, anionic and cationic surfactants. It is suitable to use an amphiphilic surfactant which may exhibit inverse solubility, and preferably a non-ionic surfactant. Non-ionic surfactants suitable for use in the present invention include alkyl ethoxylates, polyoxyethylene sorbitan fatty esters, block co-polymers, polyoxyethylene alkyl ethers, polyglycol ethers and alkyl glycosides. Preferred are surfactants containing a polyethylene glycol tail resembling the chemical structure of preferred second polymeric materials, e.g. UCON 50-HB-5100 and Breox PAG 50A 1000. Examples of alkyl ethoxylates are polyoxyethylene octylphenyl ethers, e.g. Triton® X-100 and Triton® X-114, both sold by Union Carbide in USA. Triton® X-100 and Triton® X-114, have a hydrophobic octyl-phenyl head and a hydrophilic polyoxyethylene tail, with a cloud point of 22° C. and 65° C., respectively. The cloud point for analogues can be increased by increasing the length of the hydrophilic moiety, whereas the cloud point can be decreased by increasing the length of the hydrophobic moiety. Triton® X-100 is further characterized by a HLB value of 13.5. Examples of polyoxyethylene sorbitan fatty esters are polyoxy-ethylene-(20)-sorbitan monolaurate, e.g. Tween® 80, and polyoxy-ethylene-(20)-sorbitan monooleate, e.g. Tween® 20, both sold by ICI of Great Britain. Examples of the block co-polymers are combinations of polypropyleneglycol and polyethyleneglycol, e.g. Pluronic® sold by BASF in Germany. Suitable examples of polyoxyethylene alkyl ethers are $C_{12}E_5$, $C_{12}E_8$ and Brij. A suitable example of a polyglycol ether is Tergitol.

Anionic surfactants suitable for use in the present invention include various bile acids and esters and salts thereof, such as salts of deoxycholic acid and cholic acid. Specific examples include sodium deoxycholate and sodium cholate. Further suitable anionic surfactants include salts of alkyl sulfonic acid and alkyl sulfuric acid, e.g. sodium dodecyl sulfate (SDS).

Cationic surfactants suitable for use in the present invention include salts of alkyl trimethyl ammonium, e.g. CTAB and CTAC, salts of cetylpyridinium and salts of dimethyl octadecyl ammonium.

The surfactants used in the present invention may be modified to improve their properties in the aqueous two-phase systems. For example by introducing dyes, such as Cibacron Blue. For reasons of economy and simplicity, however, it is preferred, to use surfactants which are unmodified.

The concentration of the surfactant in the primary aqueous solution may be in the range of from about 0.1 up to about 30% (w/w), suitably in the range of from 0.25 up to 20% (w/w), and preferably in the range of from 0.5 up to 10% (w/w).

It is preferred that the concentration of the surfactant in the primary aqueous solution is equal to or higher than the CMC. The CMC is primarily dependent upon the surfactant per se, the components of the solution and their concentration, the temperature and pH. The CMC of polyoxyethylene sorbitan fatty esters (polysorbates) specifically are disclosed in an article by Wan et al, J. Pharm. Sci., vol. 63, No. 1 (1974) pp. 136–137.

After the primary two-phase separation, the aqueous phase containing the main portion of the hydrophobic or amphiphilic compound and the second polymeric material and/or surfactant is removed. The hydrophobic or amphiphilic compound is thereafter separated from the second polymeric material and/or surfactant, e.g. by chromatography, such as affinity or ion-exchange chromatography, or by solvent extraction. It is also conceivable to use yet another two-phase system containing a third polymeric material or a salt, suitably an inorganic salt, for separating the second polymeric material and/or surfactant from the hydrophobic or amphiphilic compound. In a particularly preferred embodiment, however, the second polymeric material exhibits inverse solubility characteristics and the aqueous phase containing the second polymeric material and the main portion of the hydrophobic or amphiphilic compound is brought to a separation vessel for further processing.

Although various methods are available for separating the second polymeric material and/or surfactant from the hydrophobic or amphiphilic compound as is evident from the previous paragraph, the present invention will in the following be described in more detail with reference to temperature-induced phase separation with a second polymeric material exhibiting inverse solubility characteristics.

In the particularly preferred embodiment, temperature-induced phase separation is performed by heating the phase containing the main portion of the hydrophobic or amphiphilic compound to a temperature above the cloud point of the second polymeric material exhibiting inverse solubility but below the temperature where degradation of the hydrophobic or amphiphilic compounds occur. The cloud point or phase-separation temperature is a characteristic feature of polymeric materials exhibiting inverse solubility. Thus, by raising the temperature of a solution containing such a polymeric material above the cloud point, the solution becomes cloudy, owing to separation into two phases and precipitation of the polymeric material exhibiting inverse solubility. A second phase separation is hereby obtained, where a polymer-rich and a water-rich phase are formed. The water-rich phase is almost free of polymer, i.e. it commonly contains less than 1% of polymer. Conventionally, also, the polymer-rich phase forms the bottom phase after heating, since the density of the polymer-rich phase is normally higher than that of the water-rich phase. The densities can, however, be reversed by various manipulations, e.g. addition of chemicals such as urea in sufficient quantities. In the present invention, the hydrophobic or amphiphilic compounds are often almost exclusively partitioned to the water-rich phase, thereby reducing the necessity for further purification of the product at issue.

To make possible technical and economical use of polymeric materials exhibiting inverse solubility, the cloud point must be above the freezing-point of the solution and lower than 100° C. In the present invention, the cloud point of the second polymeric material exhibiting inverse solubility can be in the range of from about 5 up to about 906° C., suitably in the range of from 10 up to 756° C. Preferably, the cloud point of the second polymeric material exhibiting inverse solubility lies in the range of from 15 up to 606° C., more preferably in the range of from 20 up to 40° C.

The temperature to which the phase containing the second polymeric material must be elevated in the temperature-induced phase separation can be reduced by selecting a second polymeric material with a suitably low cloud point as is evident from the previous paragraph. However, the temperature to which the phase containing the second polymeric material must be elevated to bring about precipitation of the second polymeric material can be reduced also by adding a small amount of an organic or more commonly inorganic salt to said phase. Thus, the cloud point of UCON 50-HB-5100 being 50° C. in the absence of salt, can be lowered to e.g. 37° C. by addition of salt. It is, however, preferred that the temperature-induced phase separation is carried out in the essential absence of salt, since this facilitates the subsequent purification of the hydrophobic or amphiphilic compound.

Polymeric materials exhibiting inverse solubility and suitable for use in the present invention as the second polymeric material can be found in I. Y. Galaev et al, Enzyme Microb. Tech., vol. 15 (1993), pp. 354–366, which is hereby incorporated by reference. Specifically, polymeric materials exhibiting inverse solubility and suitable for use in the present invention as the second polymeric material include polyalkylene glycols, poly(oxyalkylene) polymers, poly(oxyalkylene) copolymers, polyvinyl pyrrolidone, polyvinyl alcohol, polyvinyl caprolactam, polyvinyl methylether, alkoxylated starches, alkoxylated cellulose, alkyl hydroxyalkyl cellulose, silicone-modified polyethers, and derivatives and mixtures thereof. Suitable polyalkylene glycols include polyethylene glycol, polypropylene glycol, and derivatives thereof, such as acrylic and methacrylic substituted polyethylene and polypropylene glycol. Suitable alkoxylated starches and alkoxylated cellulose, include methoxylated and ethoxylated starches and cellulose. Suitable alkyl hydroxyalkyl celluloses include those celluloses where the alkyl groups have from 1 up to 4 carbon atoms. A preferred alkyl hydroxyalkyl cellulose is ethyl hydroxyethyl cellulose (EHEC). Suitable poly(oxyalkylene) copolymers include random and block copolymers of ethylene oxide and propylene oxide. The hydrophobicity of the copolymers of ethylene oxide and propylene oxide increases with increasing propylene oxide content. The content of propylene oxide in the copolymer of ethylene oxide and propylene oxide suitably lies in the range of from about 30 up to about 90% by weight of the total weight of the copolymer, preferably within the range of from 40 up to 80% by weight. A specific example of a copolymer of ethylene oxide and propylene oxide suitable for use in the present invention is UCON 50-HB-5100 marketed by Union Carbide, Corp., New York City, N.Y., USA. UCON 50-HB-5100 is a random linear, non-ionic copolymer composed of 50% by weight of ethylene oxide and 50% by weight of propylene oxide, with a molecular weight ($M_r$) of 4,000 Da and a cloud point of 50° C. Another specific example of a random copolymer composed of 50% by weight of ethylene oxide and 50% by weight of propylene oxide is Breox PAG 50A 1000 marketed by International Speciality Chemicals Ltd. of Southampton, England. Breox PAG 50A 1000 has a molecular weight ($M_r$) of 3,900 Da and a cloud point of 50° C. Another example of a copolymer of ethylene oxide and propylene oxide suitable for use in the present invention is $EO_{30}PO_{70}$ which is a random copolymer composed of 30% by weight of ethylene oxide and 70% by weight of propylene oxide, with a molecular weight ($M_r$) of 3,200 Da and a cloud point of 38° C. Yet another suitable example is $EO_{20}PO_{80}$ which is a random copolymer composed of 20% by weight of ethylene oxide and 80% by weight of propylene oxide, with a molecular weight ($M_r$) of 3,300 Da and a cloud point of 25° C. in an aqueous solution containing 10% by weight of the copolymer. $EO_{30}PO_{70}$ and $EO_{20}PO_{80}$ are marketed by Shearwater Polymers, Inc., Huntsville, Ala., USA.

The Japanese patent specification with publication number JP 1994-228319 to Hidetoshi Tsuchida, discloses further polymeric materials exhibiting inverse solubility. The polymeric materials comprise block copolymers of propylene oxide and another water-soluble polymer with a molecular weight exceeding 30,000 Da. The entire content of JP 1994-228319 is hereby incorporated by reference in the present application.

The concentration of the target product in the second aqueous solution can be in the range of from about 0.1 up to about 50 g/l of the second aqueous solution, suitably within the range of from 0.5 up to 20 g/l, and preferably within the range of from 1 up to 10 g/l.

In the temperature-induced phase separation step, the more hydrophobic phase from the primary aqueous separation step is maintained for a period of time sufficient for essentially separating the hydrophobic or amphiphilic compound from the second polymeric material. This period of time can be in the range of from about 60 sec up to about 5 hours, suitably in the range of from 5 min up to 1 hour and preferably in the range of from 10 min up to 30 min. However, the period of time required for phase separation can be reduced by using e.g. centrifugal separation, centrifugal centrifugation or centrifugal decanting, before allowing the hydrophobic or amphiphilic compound to separate from the second polymeric material. If such means are employed, the period of time for separation can be in the range of from about 5 sec up to about 60 min, and suitably in the range of from 10 sec up to 30 min.

The present process can be continuous, e.g. performed on a column, or batch-wise.

The present invention can be used for purifying a wide variety of hydrophobic or amphiphilic compounds. Hydrophobic compounds are defined as compounds that are water-insoluble or slightly soluble in water in the absence of a surfactant. Amphiphilic compounds contain hydrophilic, water-soluble groups, and hydrophobic, water-insoluble or slightly water soluble groups.

The hydrophobicity can be measured as the retention coefficient of a hydrophobic or amphiphilic compound, such as a protein, in hydrophobic interaction chromatography (HIC). This can be done by using the chromatographic conditions described by Kishevarz and Nakai in Biochem. Biophys. Acta, vol. 576 (1979), pp. 269–279. The columns used were butyl- or hexylepoxy Sepharose® 4B (diameter 16 mm, 200 mm length) with equilibration and elution in 2 mM sodium phosphate buffer containing 2 M sodium chloride at a pH of 6.9. The elution was performed with a flow rate of 3 ml/(hr×cm$^2$) at 22° C. When using the analytical conditions described by Kishevarz and Nakai (see above) the hydrophobic or amphiphilic compound can have a retention coefficient equal to or greater than 1, suitably equal to or greater than 2, and preferably equal to or greater than 3.

In the present invention, hydrophobic and amphiphilic compounds also relate to chemically, physically and/or genetically modified hydrophilic compounds exhibiting hydrophobic or amphiphilic characteristics after modification. Examples of chemical and/or physical modification include introduction of covalently bound hydrophobic groups and denaturation of proteins such that the protein becomes essentially hydrophobic or amphiphilic. After altering the characteristics of the initially hydrophilic compounds and use of the present invention, the hydrophobic or amphiphilic target compounds may be made hydrophilic again.

Hydrophobic and amphiphilic compounds which may be used to advantage in the present invention include polypeptides, lipids, lipopolysaccharides, steroids, membranes, and combinations thereof. The origin of the hydrophobic or amphiphilic compound is irrelevant to the use of the present invention. The compounds may thus derive from plants or animals or may be produced initially by industrial processes. Furthermore, the compounds may be of human or animal origin or produced by recombinant DNA techniques.

In the present invention, polypeptides refer to proteins and oligopeptides with at least 5 amino acids in the chain. The number of amino acids of the polypeptide produced according to the present invention, suitably lies in the range of from 10 up to 4,500 amino acids, and preferably in the range of from 20 up to 3,000 amino acids. The polypeptides can be full-length, i.e. the sequence of amino acids is identical to the corresponding sequence found in mammals in general, and in human beings in particular. The polypeptides can also be deletion derivatives of the full-length polypeptides, where one or more amino acid is missing.

The present invention can be used to advantage for purifying compounds present in untreated fermentation broths obtained in production by recombinant DNA techniques. In the present invention, fermentation broths can contain extracellular and/or intracellular products such as proteins, as well as cellular debris, such as the cells from the starting organisms and/or cell fragments. The present invention can be used to advantage also for purifying fermentation broths which have been pretreated, e.g. by centrifugation, filtration, ultrafiltration or flocculation, for removing all or essentially all of the cellular debris.

The present invention is advantageously used for purifying any apolipoprotein A (ApoA) or Apolipoprotein E (ApoE), or variants or mixtures thereof. The present invention can be applied to ApoA or ApoE obtained from plasma, suitably human plasma, or produced by a recombinant DNA technique, suitably in gram-negative bacteria, and preferably in E. coli. The ApoA or ApoE can be unpurified, or essentially unpurified, or it can be pretreated before applying the present invention. Examples of pretreatment are diafiltration, ultrafiltration preciitation and various types of chromatography.

In the present invention, the terms ApoA and ApoE include any preform or fragment, or any truncated, extended or mutated form, or any mixture of any of these forms or fragments. Preform relates e.g. to the 249 amino acid Met form of ApoA-I as disclosed in WO-A-88/03166 assigned to Sirtori et al. Other preforms are the proapolipoprotein A-I's disclosed in U.S. Pat. No. 5,059,528 to UCB as well as EP-A-308336, JP 216988/1984 and JP 252048/1987 all to Mitsubishi Chem. Ind. Fragment relates to a part of ApoA or ApoE containing at least one α-helix, e.g. as disclosed in WO-A-93/25581 assigned to Innogenetics S.A. of Belgium. Truncated and extended forms relate to ApoA and ApoE molecules where one or more amino acids are missing or has been added, respectively, at the N and/or C terminal ends of the molecules. Suitably, from two up to eight amino acids are missing or have been added, preferably from three up to six amino acids. Mutated forms relate to ApoA and ApoE molecules where one or more amino acid has been substituted by another amino acid, e.g. ApoA-IM as disclosed in WO-A-93/12143 and WO-A-94/13819. Other mutated forms are ApoA-ISeattle (Deeb et al (1991) J. Bio. Chem. 266:13654–13660), ApoA-IYame (Takada et al (1991) J. Lipid Res. 32: 1275 ff) and a yet unnamed mutated form of ApoA-I (Matsunaga et al (1991) Proc. Natl. Acad. Sci. USA 88:2793–2797).

Human ApoE and variants thereof, are disclosed in "Human Apolipoprotein Mutants III", ed. by C. R. Sirtori et al (1993) Nato ASI Series, Springer Verlag, Berlin, II 73:81–96.

Known ApoA's are e.g. ApoA-I, ApoA-II and ApoA-IV. In the present invention, suitably, the ApoA is ApoA-I, or variants or mixtures thereof. Natural plasma ApoA-I is a single polypeptide chain of 243 amino acids, whose primary sequence is known (Brewer et al. (1978) Biochem. Biophys. Res. Commun. 80: 623–630). More suitably, the ApoA is a mutated form of ApoA-I where at least one Cys residue has been substituted for an amino acid residue, preferably an Arg residue, making formation of disulfide-linked dimer possible. In the amino acid sequence of natural human ApoA-I, Arg residues are located at positions 10, 27, 61, 83, 116, 123, 131, 149, 151, 153, 160, 171, 173, 177, 188 and 215. Of these, substitutions are preferred at one or more of positions 160, 171, 173, 177 and 188, i.e. at positions within the same α-helix. More preferably, the Arg residue is substituted at positions 171 and/or 173. Most preferably, the ApoA-I is ApoA-IM.

Human apolipoprotein A-IMilano (ApoA-IM) is a naturally occurring mutated form of normal ApoA-I (Weisgraber et al. (1980) J. Clin. Invest. 66: 901–907). In ApoA-IM, one residue of the amino acid arginine (Arg 173) has been replaced by a residue of the amino acid cysteine (Cys 173). Since ApoA-IM contains one cysteine residue per polypeptide chain, it may exist as a monomer or as a disulfide-linked dimer. The molecular weight of the monomer is about 28,000 Da and for the dimer about 56,000 Da. These two forms are chemically interchangeable, and the term ApoA-IM does not, in the present context, discriminate between the two forms.

Apo A-IM is a protein containing at least six major a-helix segments and with a very dense structure. Several of the α-helices are amphiphilic, creating an amphiphilic protein where one surface is hydrophobic and the other is hydrophilic (D. Eisenberg et al, Nature, vol. 299 (1982), pp. 371–374). The amphiphilic properties of ApoA-IM and other ApoAs create a tendency to form micellar structures with other proteins and lipids in aqueous solutions.

To make possible production of sufficient quantities of ApoA-I in general, and more specifically ApoA-IM, use is made of recombinant DNA techniques, e.g. in *E. coli*. Thus, recombinant preparation and use of ApoA-IM, monomers as well as dimers, are disclosed in patent specifications WO-A-88/03166 assigned to Parmitalia Carlo Erba (PICE), WO-A-90/12879 assigned to Sirtori et al, as well as WO-A-93/12143 and WO-A-94/13819 both assigned to Pharmacia & Upjohn AB (formerly Kabi Pharmacia AB).

The following Examples are provided for purposes of illustration only and are not to be construed as in any way limiting the scope of the present invention, which is defined by the appended claims.

The percentages and parts are per weight, unless otherwise stated.

EXPERIMENTAL

Materials

Recombinant apolipoprotein A-IM was produced in *E. coli* by Pharmacia & Upjohn AB in Stockholm, Sweden. The cells were separated and the filtrate was concentrated 4 times by ultrafiltration using a membrane with a 10,000 Da cut-off. The concentration of Apo A-IM and the total protein concentration after ultrafiltration was 3.5 mg/ml and 35 mg/ml, respectively. This material was used as starting material in Examples 1–4.

The polymers in the bottom phase were two hydroxypropyl starch polymers, Reppal PES 100 and Reppal PES 200, both obtained from Carbamyl AB of Kristianstad, Sweden, and one hydroxyethyl starch polymer, Solfarex A85 obtained from AVEBE of Vendum, the Netherlands. Reppal PES 100 and Reppal PES 200 had a molecular weight ($M_r$) of 100,000 and 200,000, respectively, and were used in pure, dry form when preparing the two-phase systems. Solfarex A85 had an undefined but higher molecular weight than Reppal PES 200. A 50% (w/w) stock solution of Solfarex A85 was heated at 80–90° C. for dissolving the hydrophilic polymer before preparing the two-phase systems.

The top-phase polymer Breox PAG 50A 1000 ($M_r$ 3,200) was obtained from International Speciality Chemicals Ltd. of Southampton, England. Breox PAG 50A 1000 has a molecular weight ($M_r$) of 3,900 Da and a cloud point of 50° C. Breox PAG 50A 1000 was used in pure, dry form when preparing the two-phase systems.

The total weight of the primary two-phase systems was 5 g. 3.75 g of the starting protein solution was added to the system, when Reppal PES 100 was used as bottom phase polymer. When Solfarex A85 was used as bottom phase polymer, the amount of protein solution added to the systems was 3.35 g.

Triton® X-100 was obtained from Boehringer Mannheim in Mannheim, Germany. Triton® X-100 is a non-ionic surfactant with a cloud point of 65° C. and a CMC of $3.1 \times 10^{-4}$ mol/l. Tween® 20 and Tween® 80 were obtained from Sigma Chemicals Co. of Saint Louis, Mo., USA. Tween® 20 is a non-ionic surfactant with a cloud point of 76° C. and a CMC of $5.9 \times 10^{-5}$ mol/l. Tween® 80 is a non-ionic surfactant with a cloud point of 65° C. and a CMC of $1.0 \times 10^{-5}$ mol/l.

All chemicals were of analytical reagent grade.

Analytical Methods and Calculations

The total protein content was determined according to Bradford, Anal. Biochem., vol. 72 (1976) pp. 248–254, using Coomassie Brilliant Blue G. The absorption was measured at 595 and 465 nm and the absorption obtained at 465 nm was then subtracted from the absorption obtained at 595 nm. Bovine serum albumin was used as standard.

The purification of Apo A-IM in the top phases was analyzed on Phast gel electrophoresis, 20% SDS-PAGE (Pharmacia & Upjohn AB, Uppsala, Sweden). The gels were stained with Coomassie Blue and scanned with a densitometer (Personal Densitometer SI, Molecular Dynamics, Sunnyvale, Calif., USA). With the help of the densitometer the percentage of Apo A-IM of the total protein concentration could be determined. This value was used to calculate the degree of purification:

$$\text{Degree of purification} = P^s{}_{Apo}/P_{Apo} \qquad (3)$$

wherein $P^s{}_{Apo}$=percentage of Apo A-IM of the total protein in the sample $P_{Apo}$=percentage of Apo A-IM of the total protein in the starting material The top height was used to calculate the yield. Adjustments for the volume change and the dilution of the samples were made.

$$\text{Yield}=(\text{top height} \times V^t \times \text{dilution})_{sample}/(\text{top height} \times V \times \text{dilution})_{starting\ material} \times 100 \qquad (4)$$

wherein $V^t$=volume of the water-rich top phase after thermal separation

V=volume of the starting material added to the two phase system.

The yield of Apo A-IM can also be calculated as:

$$\text{Yield}=(C^t{}_{Apo} * V^t)/(C_{Apo} * V) \times 100 \qquad (5)$$

wherein $C^t{}_{Apo}$=concentration of Apo A-IM in the water-rich top phase after thermal separation $C_{Apo}$=concentration of Apo A-IM in the starting material $V^t$=volume of the water-rich top phase after thermal separation and V=volume of the starting material added to the two phase system.

The degree of purification of Apo A-1M in the systems can be also calculated as:

$$\text{Degree of purification}=(C^t{}_{Apo}/C^t)/(C_{Apo}/C) \qquad (6)$$

wherein $C^t{}_{Apo}$=concentration of Apo A-IM in the water-rich top phase after thermal separation $C_{Apo}$=concentration of Apo A-IM in the starting material $C^t$=total protein concentration in the water-rich top phase after thermal separation and C=total protein concentration in the starting material.

The polymer concentrations were calculated as % weight/weight (w/w).

In the experiments with recycling of top-phase copolymer and surfactant the top phase from the primary system was removed after phase separation and weighed. After thermal separation the phases were isolated and weighed again. The top phases were analyzed for Triton® X-100 content by measuring the absorption at 275 nm. The Breox PAG 50A 1000 concentration was calculated by measuring the refractive index and subtracting the part that came from Triton® X-100. In this way the recovery of the polymer and surfactant could be determined.

EXAMPLE 1

The effect on purification and yield of primary aqueous two-phase separation followed by temperature-induced phase separation was studied using Apo A-IM as target protein. After cell removal, an *E. coli* fermentation solution containing Apo A-IM was added to an aqueous solution containing Reppal PES 100, Breox PAG 50A 1000 and Triton® X-100. The resulting primary aqueous solution containing 8% Reppal PES 100, 16% Breox PAG 50A 1000 and 0 to 4.0% (w/w) Triton® X-100 was mixed with a magnetic stirrer. The temperature in the primary aqueous solution was 22° C. The separation into two phases was enhanced by centrifuging at 1,360 g for 10 min. After phase separation in the primary aqueous system, temperature-induced phase separation was performed by maintaining the isolated top phase at 60° C. for 30 min.

Triton® X-100 was partitioned primarily to the top phase, the partition coefficient K being 5.5 as calculated according to formula (1), at a surfactant concentration of 1.0% (w/w).

The degree of purification and yield of Apo A-IM after separation from Reppal PES 100 in the primary aqueous two-phase step, and from Breox PAG 50A 1000 and Triton® X-100 in the temperature-induced phase separation, are evident from Table I. The degree of purification and yield were determined by gel scanning with densitometer.

TABLE I

Effect of surfactant concentration in a primary aqueous two-phase step on yield and purification of Apo A-1M after a subsequent thermal separation step.

| Test | Surfactant conc. (%) | Degree of purification | Yield (%) |
|---|---|---|---|
| Comparative | 0.0 | 1.4 | 8 |
| 1 | 0.25 | 6.7 | 69 |
| 2 | 0.5 | 6.8 | 77 |
| 3 | 1.0 | 6.7 | 88 |
| 4 | 2.0 | 5.7 | 91 |
| 5 | 4.0 | 5.5 | 88 |

As is evident from Table I, use of a composition containing a surfactant and a first and a second polymeric material in the primary aqueous two-phase step dramatically improves the resulting yield and purity of Apo A-1M after a subsequent thermal separation step as compared with the comparative experiment, where the surfactant was lacking in the primary aqueous two-phase step.

EXAMPLE 2

The process according to Example 1 was repeated with the difference that two hydrophilic polymeric materials and three different surfactants with varying concentrations were used. The primary aqueous two-phase solution contained 8% Reppal PES 100 or 8% Solfarex A85, 16% Breox PAG 50A 1000 and 1.0% Triton® X-100, 2.0% Tween® 80 or 2.0% Tween® 20. The results are shown in Table II.

TABLE II

The effect of surfactant and bottom-phase polymer on yield and purification of Apo A-1M after a subsequent thermal separation step.

| Surfactant and conc. (%) | Reppal PES 100 Degree of purification | Reppal PES 100 Yield (%) | Solfarex A85 Degree of purification | Solfarex A85 Yield (%) |
|---|---|---|---|---|
| Triton ® X-100 1.0% | 7.2 | 85 | 7.0 | 77 |
| Tween ® 80 2.0% | 7.5 | 54 | 5.5 | 45 |
| Tween ® 20 2.0% | 7.4 | 40 | 6.5 | 54 |

As is evident from Table II, use of the inventive compositions containing various surfactants and concentrations and various first polymeric materials, can be used to improve the resulting yield and purity of Apo A-1M after a subsequent thermal separation step.

EXAMPLE 3

The effect of surfactant on partitioning coefficient, K, and the distribution ratio, G, for Apo A-1M and total protein in a primary aqueous two-phase step was studied in a primary aqueous solution containing 6% Reppal PES 100 and 12% Breox PAG 50A 1000, in combination with 1% Triton® X-100, 2% Tween® 80 or without surfactant for comparison, respectively.

The bulk *E. coli* proteins were strongly partitioned to the bottom phase in all three systems. In the systems with surfactant, Apo A-IM was partitioned to the to p phase. The partitioning coefficient, K, and the distribution ratio, G, for Apo A-IM and total protein calculated according to formulas (1) and (2) and based on ELISA results are shown in Table III.

TABLE III

The effect of surfactant on partitioning coefficient, K, and the distribution ratio, G, for Apo A-1M and total protein in a primary aqueous two-phase step.

| Surfactant and conc. (%) | $V_{Top}/V_{Bottom}$ | $K_{protein}$ | $G_{protein}$ | $K_{Apo\ A-1M}$ | $G_{Apo\ A-1M}$ |
|---|---|---|---|---|---|
| — 0% | 6.0 | 0.07 | 0.39 | 1 | 6 |
| Triton ® X-100 1.0% | 4.1 | 0.11 | 0.49 | 7 | 29 |
| Tween ® 80 2.0% | 4.5 | 0.10 | 0.50 | 4 | 18 |

As is evident from Table III, the partitioning coefficient, K, and the distribution ratio, G, are dramatically increased for the target compound Apo A-IM when a surfactant is present in the primary aqueous solution.

EXAMPLE 4

The influence of aqueous two-phase separation with a surfactant followed by a thermal separation step on removal of contaminating nucleic acids was studied using Apo A-IM as target protein. The process according to Example 2 was repeated with 6% Reppal PES 100, 12% Breox PAG 50A 1000 and 2% Tween® 80. The results are shown in Table IV.

TABLE IV

The effect of an aqueous two-phase step with a surfactant followed by a thermal separation step on removal of DNA.

| Sample | DNA conc. (μg/ml) | Degree of DNA removal |
|---|---|---|
| Starting material | 2.1 | — |
| Water-rich top phase after thermal separation | <0.002 | >1,000 |

As is evident from Table IV, the resulting DNA concentration in the final protein-containing water phase was reduced more than 1,000 times, when compared with the starting material.

EXAMPLE 5

The effect of recycling of surfactant and top-phase polymer after temperature-induced phase separation was studied using Apo A-IM as target compound. The process sequence including recycling is schematically illustrated in FIG. 1. The process according to Example 1 was repeated with the difference that the proteineous starting material contained 0.9 mg/ml of Apo A-IM and 7 mg/ml of total protein. Furthermore, the primary aqueous two-phase solution contained 17% Reppal PES 200,12% Breox PAG 50A 1000 and 1% Triton® X-100. The lower phase obtained after temperature-induced phase separation containing Breox PAG 50A 1000 and Triton® X-100 was separated from the upper phase containing Apo A-IM. The solution containing Breox PAG 50A 1000 and Tritone X-100 was recycled to the primary aqueous two-phase system. The concentration of Breox PAG 50A 1000 and Triton® X-100 in the recycled solution were 55% (w/w) and 4.9% (w/w), respectively. The primary aqueous two-phase system was prepared from a new protein start solution by adding about 10–15% of the original amount of Breox PAG 50A 1000 and Triton® X-100 to make up for the losses in each cycle. The bottom-phase polymer constituted 100% fresh Reppal PES 200 in each cycle.

The average recovery of Breox PAG 50A 1000 and Triton® X-100 in each cycle was 83% and 88%, respectively.

The partitioning of Triton® X-100 was determined after temperature-induced phase separation at 60° C. Triton® X-100 partitioned strongly to the copolymer-containing bottom phase with a partitioning coefficient, K, of 0.004. The top phase containing essentially water and protein contained 0.02% Triton® X-100 as measured by spectrophotometry. The copolymer-surfactant phase obtained after heating to 60° C. had a concentration of 55% Breox 50A1000 and 4.9% Triton X-100.

When samples from the copolymer-surfactant phase were analyzed with SDS-PAGE and stained with silver nitrate, no protein could be detected, i.e. no detectable Apo A-IM was lost in the recycled phase even after recycling at least three times.

The degree of purification and yield of Apo A-IM after temperature-induced phase separation are evident from Table V. The degree of purification and yield were calculated according to formulas (5) and (6) based on ELISA results.

TABLE V

Effect of recycling of surfactant and second polymeric material on yield and purification of Apo A-1M in an aqueous two-phase step followed by a thermal separation step.

| Recycling times | Degree of purification | Yield (%) |
|---|---|---|
| 0 | 4.2 | 76 |
| 1 | 4.6 | 74 |
| 2 | 4.5 | 72 |
| 3 | 4.5 | 76 |

As is evident from Table V, the degree of purification and yield of Apo A-IM in the systems with recycled top-phase polymer and surfactant were equal to the initial aqueous two-phase system with new polymers and surfactant.

EXAMPLE 6

The effect of recycling of surfactant and top-phase polymer after temperature-induced phase separation was studied using Apo A-IM as target compound. The process according to Example 5 was repeated with the difference that $EO_{30}PO_{70}$ was used as second polymeric material instead of Breox PAG 50A 1000. The same concentrations of polymers and surfactant were used. The concentration of $EO_{30}PO_{70}$ and Triton® X-100 in the recycled solution were 80% (w/w) and 6.3% (w/w), respectively. The degree of purification and yield of Apo A-IM after temperature-induced phase separation are evident from Table VI. The degree of purification and yield were calculated according to formulas (5) and (6) based on ELISA results.

TABLE VI

Effect of recycling of surfactant and second polymeric material on yield and purification of Apo A-1M in an aqueous two-phase step followed by a thermal separation step.

| Recycling times | Degree of purification | Yield (%) |
|---|---|---|
| 0 | 5.4 | 76 |
| 1 | 4.8 | 53 |
| 2 | 5.5 | 74 |
| 3 | 4.6 | 54 |

As is evident from Table VI, the degree of purification and yield of Apo A-IM in the systems with recycled top-phase polymer and surfactant can be equal to the initial aqueous two-phase system with new polymers and surfactant.

What is claimed is:

1. A process for purifying an apolipoprotein, comprising
   a) mixing, in arbitrary order, a starting material containing the apolipoprotein, a first hydrophilic polymeric material, water, a second amphiphilic polymeric material and a surfactant, the first polymeric material and the second polymeric material being immiscible in the resulting primary aqueous solution, the first polymeric material comprising hydroxyalkyl starch, the second polymeric material comprising poly(oxyalkylene) copolymer, and the surfactant comprising alkyl ethoxylate;
   b) maintaining the primary aqueous solution for a period of time sufficient for essentially separating the solution into phases;
   c) removing a phase containing a main portion of the apolipoprotein and the second polymeric material;

d) separating the apolipoprotein from the second polymeric material; and subsequently e) recycling the separated second polymeric material to the initial mixing step (a).

2. A process according to claim 1, wherein the first polymeric material, the second polymeric material and the surfactant are mixed with water and the starting material containing the apolipoprotein.

3. A process according to claim 1, wherein the molecular weight of the first polymeric material lies in the range of from about 5,000 up to about 5,000,000 Da.

4. A process according to claim 1, wherein the second polymeric material exhibits inverse solubility characteristics.

5. A process according to claim 4, wherein the second polymeric material has a cloud point in the range of from about 5° C. up to about 90° C.

6. A process according to claim 1, wherein the poly (oxyalkylene) copolymer is a random or block copolymer of ethylene oxide and propylene oxide.

7. A process according to claim 6, wherein the content of propylene oxide of the copolymer lies in the range of from about 30% to about 90% by weight of the total weight of the copolymer.

8. A process according to claim 4, wherein the apolipoprotein is separated from the second polymeric material by heating the removed phase to a temperature below the temperature where degradation of the apolipoprotein occurs but above the cloud point of the second polymeric material for precipitating the second polymeric material, and subsequently separating a phase containing the precipitated second polymeric material from a phase containing the apolipoprotein.

9. A process according to claim 1, wherein the concentration of the first polymeric material in the primary aqueous solution lies in the range of from about 1% to about 30% by weight of the total weight of the primary aqueous solution.

10. A process according to claim 1, wherein the concentration of the second polymeric material in the primary aqueous solution lies in the range of from about 0.5% to about 30% by weight of the total weight of the primary aqueous solution.

11. A process according to claim 1, wherein the concentration of the apolipoprotein in the primary aqueous solution lies in the range of from about 0.1 g/l to about 50 g/l of the primary aqueous solution.

12. A process according to claim 1, wherein the concentration of the surfactant in the primary aqueous solution is above the critical micelle concentration (CMC).

13. A process according to claim 1, wherein at least about 60% of the initial amount of the second polymeric material is recycled to the initial mixing step.

14. A process according to claim 1, wherein the apolipoprotein is apolipoprotein A (ApoA), apolipoprotein E (ApoE), or variants or mixtures thereof.

15. A process according to claim 14 wherein the ApoA or ApoE is produced by recombinant DNA technique.

16. A process according to claim 14, wherein the ApoA or ApoE is obtained from human plasma.

17. A process according to claim 14, wherein the ApoA is ApoA-I, or variants or mixtures thereof.

18. A process according to claim 17, wherein the ApoA-I is ApoA-IMilano.

19. A process according to claim 3, wherein the molecular weight of the first polymeric material lies in the range of from 40,000 to 500,000 Da.

20. A process according to claim 5, wherein the second polymeric material has a cloud point in the range of from 15° C. to 60° C.

21. A process according to claim 7, wherein the content of propylene oxide of the copolymer lies in the range of from 40% to 80% by weight of the total weight of the copolymer.

22. A process according to claim 9, wherein the concentration of the first polymeric material in the primary aqueous solution lies in the range of from 3% to 20% by weight.

23. A process according to claim 10, wherein the concentration of the second polymeric material in the primary aqueous solution lies in the range of from 3% to 20% by weight of the total weight of the primary aqueous solution.

24. A process according to claim 11, wherein the concentration of the apolipoprotein in the primary aqueous solution lies in the range of from 1 g/l to 10 g/l of the primary aqueous solution.

25. A process according to claim 13, wherein at least 80% of the initial amount of the second polymeric material is recycled to the initial mixing step.

26. A process according to claim 1, wherein the primary aqueous solution essentially separates into two phases.

27. A process for purifying an apolipoprotein, comprising a) mixing, in arbitrary order, a starting material containing the apolipoprotein, a first hydrophilic polymeric material, water, a second amphiphilic polymeric material and a surfactant, the first polymeric material and the second polymeric material being immiscible in the resulting primary aqueous solution material comprising hydroxyvalkyl starch, the second polymeric material comprising poly(oxyalkylene) copolymer, and the surfactant comprising alkyl ethoxylate;

b) maintaining the primary aqueous solution for a period of time sufficient for essentially separating the solution into phases;

c) removing a phase containing a main portion of the apolipoprotein, the second polymeric material and the surfactant;

d) separating the apolipoprotein from the second polymeric material and the surfactant; and subsequently e) recycling the second polymeric material and the surfactant to the initial mixing step (a).

28. A process according to claim 27, wherein the second polymeric material exhibits inverse solubility characteristics.

29. A process according to claim 23, wherein the second polymeric material has a cloud point in the range of from about 5° C. to about 90° C.

30. A process according to claim 27, wherein the poly (oxyalkylene) copolymer is a random or block copolymer of ethylene oxide and propylene oxide.

31. A process according to claim 27, wherein the primary aqueous solution essentially separates into two phases.

32. A process for purifying an apolipoprotein, comprising a) mixing, in arbitrary order, a starting material containing the apolipoprotein, a first hydrophilic polymeric material, water and a surfactant, the first polymeric material and the surfactant being immiscible in the resulting primary aqueous solution, the first polymeric material comprising hydroxyalkyl starch, the second polymeric material comprising poly(oxyalkylene) copolymer, and the surfactant comprising alkyl ethoxylate;

b) maintaining the primary aqueous solution for a period of time sufficient for essentially separating the solution into two phases;

c) removing a phase containing a main portion of the apolipoprotein and the surfactant;

d) separating the apolipoprotein from the surfactant; and subsequently e) recycling the surfactant to the initial mixing step (a).

* * * * *

UNITED STATES PATENT AND TRADEMARK OFFICE
CERTIFICATE OF CORRECTION

PATENT NO.     : 6,107,467
DATED          : August 22, 2000
INVENTOR(S)    : Hans Ageland It is certified that error appears in the above-identified patent and that said Letters Patent is hereby corrected as shown below:

Claim 27, column 22,
Line 23, after "solution", insert -- , the first polymeric. --
Line 24, change "hydroxyvalkyl" to -- hydroxyalkyl -- .

Signed and Sealed this

Fourth Day of September, 2001

Attest:

Nicholas P. Godici

*Attesting Officer*

NICHOLAS P. GODICI
*Acting Director of the United States Patent and Trademark Office*